US00PP18002P2

(12) United States Plant Patent
Asano

(10) Patent No.: US PP18,002 P2
(45) Date of Patent: Sep. 11, 2007

(54) ***OSTEOSPERMUM* PLANT NAMED 'SPARK ORANGE'**

(50) Latin Name: *Osteospermum ecklonis*
Varietal Denomination: Spark Orange

(76) Inventor: Toshiharu Asano, 323 Hikie, Gifu-shi, Gifu-ken (JP)

( * ) Notice: Subject to any disclaimer, the term of this patent is extended or adjusted under 35 U.S.C. 154(b) by 0 days.

(21) Appl. No.: 11/406,001

(22) Filed: Apr. 18, 2006

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Osteospermum* plant named 'Spark Orange', characterized by its upright and compact plant habit; vigorous growth habit; light green-colored leaves; freely flowering habit; and daisy-type inflorescences with intense orange-colored ray florets.

2 Drawing Sheets

Botanical designation: *Osteospermum ecklonis.*
Cultivar denomination: 'Spark Orange'.

BACKGROUND OF THE INVENTION

The present invention relates to a new and distinct cultivar of *Osteospermum* plant, botanically known as *Osteospermum ecklonis,* and hereinafter referred to by the name 'Spark Orange'.

The new *Osteospermum* is a naturally-occurring whole plant mutation of the *Osteospermum ecklonis* cultivar Julie, not patented. The new *Osteospermum* was discovered and selected by the Inventor as a single flowering plant within a population of plants of the cultivar Julie in a controlled environment in Gifu, Japan in February, 2003. The selection of this plant was based on its attractive ray floret coloration.

Asexual reproduction of the new cultivar by terminal vegetative cuttings in a controlled environment in Gifu, Japan since April, 2003, has shown that the unique features of this new *Osteospermum* are stable and reproduced true to type in successive generations.

SUMMARY OF THE INVENTION

The cultivar Spark Orange has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Spark Orange'. These characteristics in combination distinguish 'Spark Orange' as a new and distinct cultivar of *Osteospermum:*

1. Upright and compact plant habit.
2. Vigorous growth habit.
3. Light green-colored leaves.
4. Freely flowering habit.
5. Daisy-type inflorescences with intense orange-colored ray florets.

In side-by-side comparisons conducted in Gifu, Japan, plants of the new *Osteospermum* differed from plants of the parent, the cultivar Julie, in the following characteristics:

1. Plants of the new *Osteospermum* were more vigorous than plants of the cultivar Julie.
2. Plants of the new *Osteospermum* had curled leaves whereas plants of the cultivar Julie had flat leaves.
3. Plants of the new *Osteospermum* and the cultivar Julie differed in ray floret coloration as plants of the cultivar Julie had light orange-colored ray florets.

Plants of the new *Osteospermum* can be compared to plants of the *Osteospermum* cultivar Mikey, not patented. In side-by-side comparisons conducted in Gifu, Japan under natural season conditions, plants of the new *Osteospermum* differed from plants of the cultivar Mikey in the following characteristics:

1. Plants of the new *Osteospermum* were more vigorous than plants of the cultivar Mikey.
2. Plants of the new *Osteospermum* had curled leaves whereas plants of the cultivar Mikey had flat leaves.
3. Plants of the new *Osteospermum* and the cultivar Mikey differed in ray floret coloration as plants of the cultivar Mikey had yellow-colored ray florets.

BRIEF DESCRIPTION OF THE PHOTOGRAPHS

The accompanying photographs illustrate the overall appearance of the new *Osteospermum.* These photographs show the colors as true as it is reasonably possible to obtain in colored reproductions of this type. Colors in the photographs may differ slightly from the color values cited in the detailed botanical description which accurately describe the colors of the new *Osteospermum.*

The photograph on the first sheet comprises a side perspective view of a typical flowering plant of 'Spark Orange' grown in a container.

The photograph on the second sheet comprises a close-up view of a typical inflorescence of 'Spark Orange'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Japan during the winter and early spring in a polyethylene-covered greenhouse and under conditions and practices which approximate those generally used in commercial *Osteospermum* production. During the production of the plants, day temperatures ranged from 10° C. to 30° C. and night ranged from 8° C. to 12° C. Measurements and numerical values represent averages for typical flowering plants. Plants were about four to five months old when the photographs and description were taken.

Botanical classification: *Osteospermum ecklonis* cultivar Spark Orange.

Parentage: Naturally-occurring whole plant mutation of *Osteospermum ecklonis* cultivar Julie, not patented.

Propagation:

*Type.*—Terminal vegetative cuttings.

*Time to initiate roots.*—About two to three weeks.

*Time to produce a rooted cutting.*—About three to four weeks.

*Root description.*—Medium in thickness; white in color.

*Rooting habit.*—Moderately branching.

Plant description:

*Plant form/growth habit.*—Upright and compact plant habit. Columnar with inflorescences positioned well above the foliar plane. Vigorous growth habit.

*Plant height* (*soil level to top of foliar plane*).—About 12 cm.

*Plant height* (*soil level to top of inflorescences*).—About 20 cm.

*Plant diameter.*—About 13 cm.

*Lateral branches.*—Length: About 7 cm. Diameter: About 1 cm. Internode length: About 5 mm. Strength: Strong. Texture: Slightly pubescent. Color: 145A.

*Foliage description.*—Length: About 5.5 cm. Width: About 2 cm. Shape: Spatulate, elongated; sessile. Apex: Obtuse. Base: Acute. Margin: Serrated. Texture, upper and lower surfaces: Smooth, glabrous. Color: Developing foliage, upper surface: 137C. Developing foliage, lower surface: 146C. Fully expanded foliage, upper and lower surfaces: 146C; venation, 145A.

Inflorescence description:

*Appearance.*—Daisy-type inflorescence form with elongated oblong-shaped ray florets. Inflorescences positioned above the foliage, arising from leaf axils. Disc and ray florets developing acropetally on a capitulum. Inflorescences face mostly upright. Freely flowering habit; about four to five inflorescences develop per plant. Inflorescences persistent. Inflorescences not fragrant.

*Flowering response.*—Under natural season conditions, plants flower in March and April.

*Inflorescence bud.*—Height: About 1.5 cm. Diameter: About 1 cm. Shape: Oblate. Color: Close to 144A.

*Inflorescence size.*—Diameter: About 6 cm. Depth (height): About 1.8 cm. Disc diameter: About 1 cm. Receptacle diameter: About 9 mm. Receptacle height: About 3 mm.

*Ray florets.*—Shape: Elongated oblong. Length: About 3 cm. Width: About 8 mm. Apex: Emarginate. Margin: Entire: Texture: Smooth, glabrous. Orientation: Upright. Number of ray florets per inflorescence: About 21 in a single whorl; florets imbricate. Color: When opening and fully opened, upper surface: 28A; towards the base, 89A. When opening and fully opened, lower surface: 25A.

*Disc florets.*—Shape: Tubular; apex dentate, five-pointed. Length: About 6 mm. Diameter, apex: About 1.5 mm. Diameter, base: About 0.5 mm. Number of disc florets per inflorescence: About 50. Color: Immature: 95A. Mature: Apex: 95A. Mid-section and base: 145D.

*Phyllaries.*—Quantity per inflorescence: About 20. Length: About 1.2 cm. Width: About 2 mm. Shape: Linear. Apex: Acuminate. Base: Obtuse, fused. Margin: Entire. Texture, upper and lower surfaces: Smooth. Color, upper surface: 137A. Color, lower surface: 139C.

*Peduncles.*—Length: About 6.2 cm. Diameter: About 2 mm. Shape: Moderately strong. Aspect: Mostly upright. Texture: Rough. Color: 144B.

*Reproductive organs.*—Androecium: Present on disc florets only. Anther shape: Oblong. Anther length: About 1 mm. Anther color: Purplish. Pollen amount: Moderate. Pollen color: Orange. Gynoecium: Present on both ray and disc florets. Pistil length: About 5 mm. Stigma color: Purplish. Style color: Purplish.

*Seed/fruit.*—Seed and fruit production has not been observed.

Disease/pest resistance: Plants of the new *Osteospermum* have not been shown to be resistant to pathogens and pests common to *Osteospermums*.

Temperature tolerance: Plants of the new *Osteospermum* have been observed to tolerate temperatures ranging from about 3° C. to about 35° C.

It is claimed:

1. A new and distinct *Osteospermum* plant named 'Spark Orange', as illustrated and described.

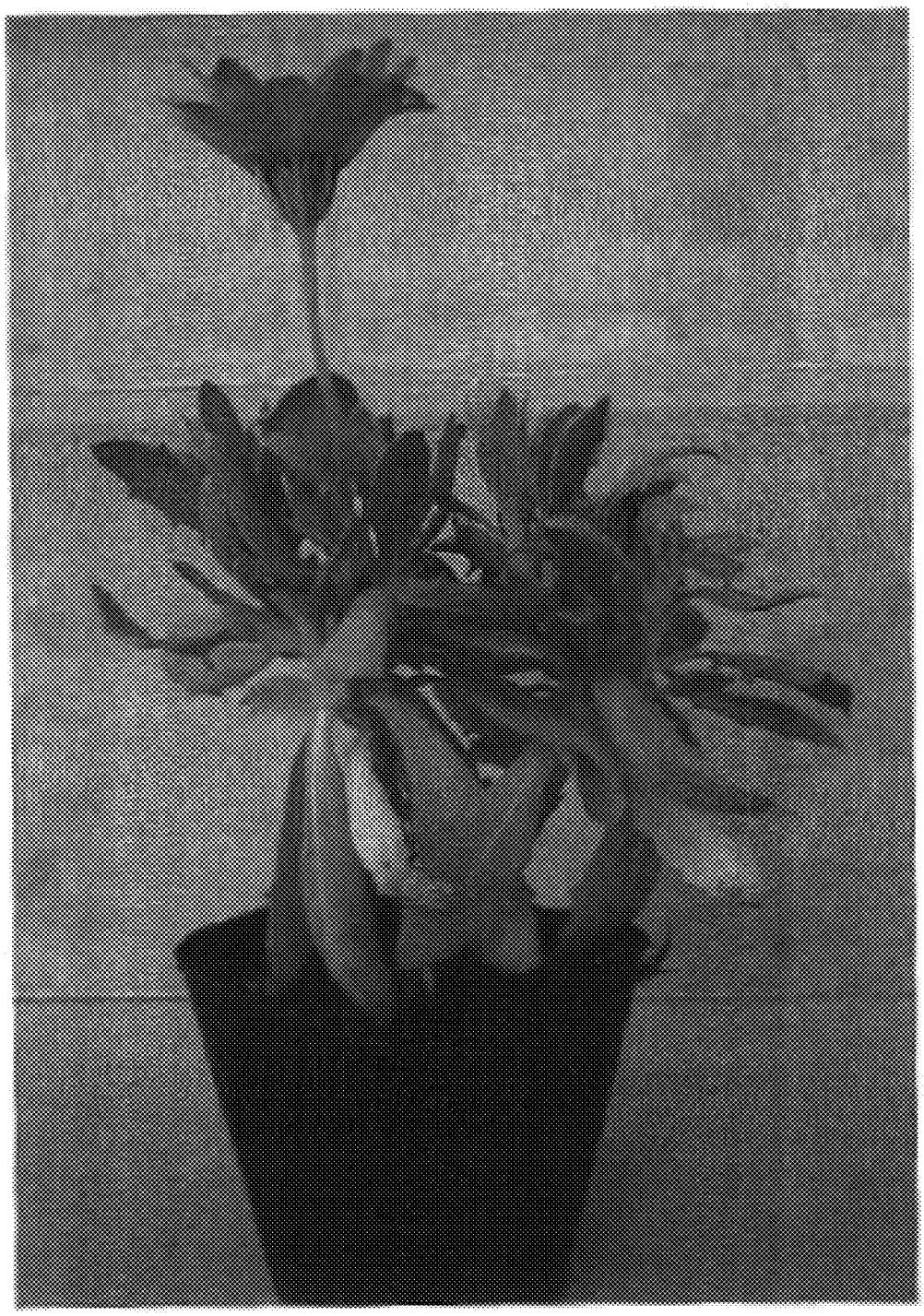

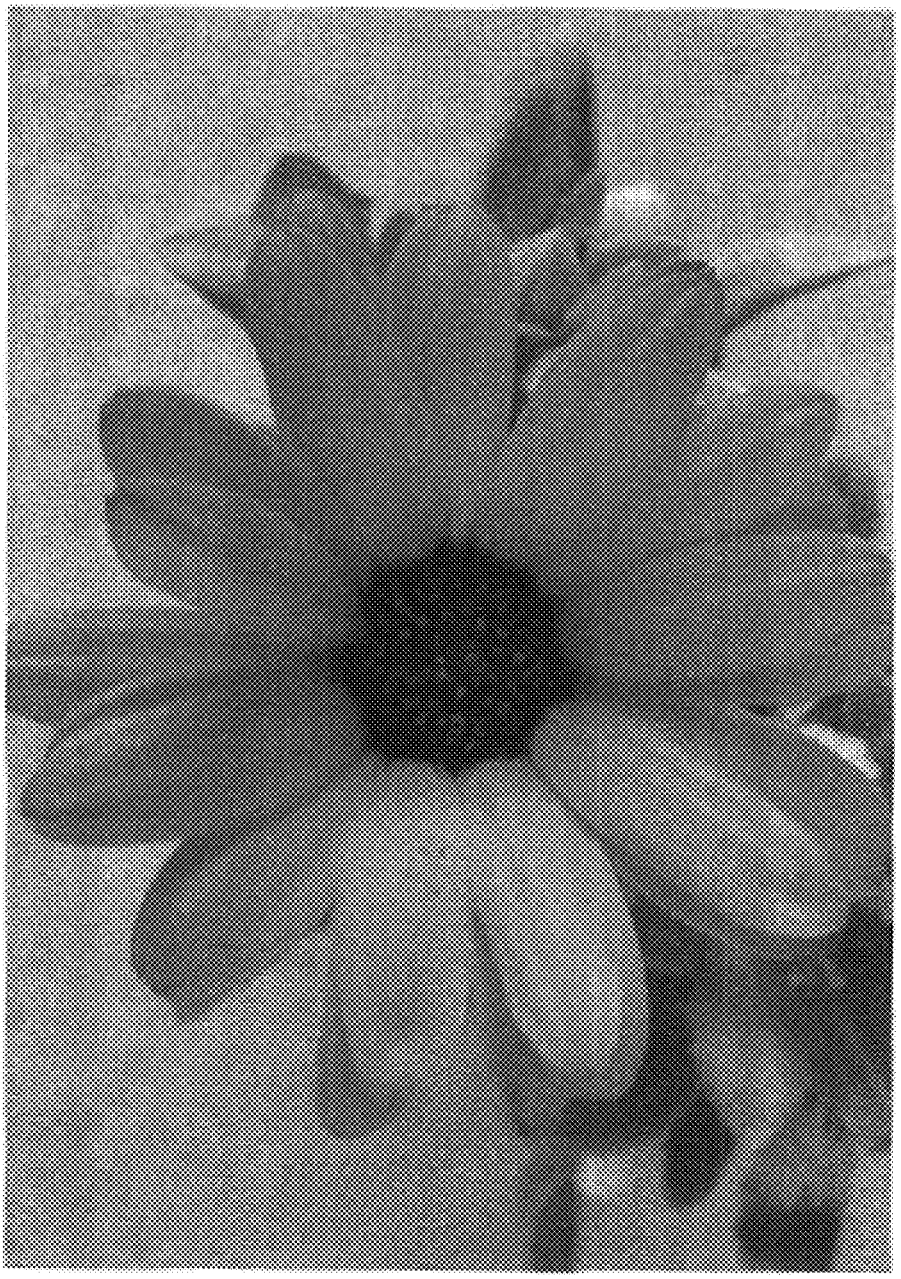

* * * * *